United States Patent
Strul

(10) Patent No.: US 6,682,527 B2
(45) Date of Patent: Jan. 27, 2004

(54) METHOD AND SYSTEM FOR HEATING TISSUE WITH A BIPOLAR INSTRUMENT

(75) Inventor: Bruno Strul, Portola Valley, CA (US)

(73) Assignee: Perfect Surgical Techniques, Inc., Santa Clara, CA (US)

( * ) Notice: Subject to any disclaimer, the term of this patent is extended or adjusted under 35 U.S.C. 154(b) by 506 days.

(21) Appl. No.: 09/808,096

(22) Filed: Mar. 13, 2001

(65) Prior Publication Data

US 2002/0133152 A1 Sep. 19, 2002

(51) Int. Cl.⁷ .................................. A61B 18/18
(52) U.S. Cl. ................ 606/51; 606/52; 606/34; 606/38
(58) Field of Search .................. 606/51, 33, 45, 606/52, 34, 41, 48, 49, 50, 37, 38

(56) References Cited

U.S. PATENT DOCUMENTS

| | | |
|---|---|---|
| 4,016,886 A | 4/1977 | Doss et al. |
| 4,043,342 A | 8/1977 | Morrison, Jr. |
| 5,098,431 A | 3/1992 | Rydell |
| 5,151,102 A | 9/1992 | Kamiyama et al. |
| 5,217,460 A | 6/1993 | Knoepfler |
| 5,370,645 A | 12/1994 | Klicek et al. |
| 5,383,876 A | 1/1995 | Nardella |
| 5,403,312 A | 4/1995 | Yates et al. |
| 5,437,664 A | 8/1995 | Cohen et al. |
| 5,441,499 A | 8/1995 | Fritzsch |
| 5,445,638 A | 8/1995 | Rydell et al. |
| 5,496,312 A | 3/1996 | Klicek |
| 5,514,129 A | 5/1996 | Smith |
| 5,527,313 A | 6/1996 | Scott et al. |
| 5,556,396 A | 9/1996 | Cohen et al. |
| 5,558,671 A | 9/1996 | Yates |
| 5,582,611 A | 12/1996 | Tsuruta et al. |
| 5,599,344 A | 2/1997 | Paterson |
| 5,655,085 A | 8/1997 | Ryan et al. |
| 5,662,680 A | 9/1997 | Desai |
| 5,688,270 A | 11/1997 | Yates et al. |
| 5,693,051 A | 12/1997 | Schulze et al. |
| 5,695,494 A | 12/1997 | Becker |
| 5,702,390 A | 12/1997 | Austin et al. |
| 5,772,659 A | 6/1998 | Becker et al. |
| 5,776,130 A | 7/1998 | Buysse et al. |
| 5,797,941 A | 8/1998 | Schulze et al. |
| 5,827,271 A | 10/1998 | Buysse et al. |
| 5,833,690 A | 11/1998 | Yates et al. |
| 5,954,717 A | 9/1999 | Behl et al. |

(List continued on next page.)

FOREIGN PATENT DOCUMENTS

| | | |
|---|---|---|
| FR | 598149 | 5/1925 |
| SU | 197711 | 8/1967 |
| WO | WO 93/08757 | 5/1993 |
| WO | WO 95/09577 | 4/1995 |
| WO | WO 95/20360 | 8/1995 |

*Primary Examiner*—Sang Y. Paik
*Assistant Examiner*—Fadi H. Dahbour
(74) *Attorney, Agent, or Firm*—Townsend and Townsend and Crew LLP

(57) ABSTRACT

Methods for heating tissue completely, thoroughly, and uniformly comprise delivering radio frequency energy through a bipolar surgical instrument having first and second jaws with first and second electrode members within the treatment region. Tissue is grasped between the first and second jaws of the bipolar instrument. The electrode members are energized at a power level to deliver electrical energy to and heat tissue between the first and second electrode members. The power level is increased at a predetermined rate from an initial level. The initial level and predetermined rate are selected to avoid creating a vapor layer and to permit an impedance increase to occur as a result of complete tissue desiccation. A tissue impedance may also be measured and compared to a preset impedance limit for terminating the power delivery when the measured impedance exceeds the impedance limit.

30 Claims, 6 Drawing Sheets

U.S. PATENT DOCUMENTS

| | | | | |
|---|---|---|---|---|
| 6,030,384 A | * | 2/2000 | Nezhat | 606/48 |
| 6,033,399 A | | 3/2000 | Gines | |
| 6,123,701 A | * | 9/2000 | Nezhat | 606/33 |
| 6,132,429 A | | 10/2000 | Baker | |
| 6,162,220 A | | 12/2000 | Nezhat | |
| 6,478,794 B1 | * | 11/2002 | Trapp et al. | 606/45 |
| 6,482,205 B1 | * | 11/2002 | Bonnet | 606/51 |
| 6,514,252 B2 | * | 2/2003 | Nezhat et al. | 606/48 |
| 6,520,960 B2 | * | 2/2003 | Blocher et al. | 606/51 |
| 6,524,309 B1 | * | 2/2003 | Watrelot et al. | 606/51 |
| 6,585,735 B1 | * | 7/2003 | Frazier et al. | 606/51 |
| 6,616,662 B2 | * | 9/2003 | Scholer et al. | 606/51 |

* cited by examiner

METHOD AND SYSTEM FOR HEATING TISSUE WITH A BIPOLAR INSTRUMENT

BACKGROUND OF THE INVENTION

1. Field of the Invention

The present invention relates generally to the use of radio frequency energy for heating and desiccating tissue. More particularly, the present invention relates to a control method, system, and apparatus for delivering radio frequency current to the tissue through electrodes disposed on bipolar surgical instruments.

The delivery of bipolar radio frequency energy to target regions within tissue is known for a variety of purposes. Of particular interest to the present invention, radio frequency energy may be delivered by bipolar surgical instruments to regions in target tissue for the purpose of heating and/or desiccation, referred to generally as hyperthermia. Bipolar electrosurgical devices rely on contacting electrodes of different polarity in close proximity to each other against or into tissue. For example, bipolar forceps have been used for coagulating, cutting, and desiccating tissue, where opposed jaws of the forceps are connected to different poles of an electrosurgical power supply. The radio frequency current thus flows from one jaw to the other through the tissue present therebetween. Use of such bipolar forceps is effective for a number of purposes and advantageous in that its effect is generally limited to the tissue held between the jaws without unwanted heating of adjacent tissues.

A primary goal for the delivery of bipolar radio frequency energy for hyperthermic treatments is the complete, thorough, and uniform heating of the treatment tissue without causing charring of the treatment tissue. Charring greatly increases electrical resistance through the tissue prematurely and can result in termination of the treatment before the tissue is uniformly heated. Uniform heating of the target tissue, however, can be difficult to achieve, particularly in highly vascularized tissues where the variability in local blood flow can have a significant effect on the heating characteristics of the tissue. For example, creation of a lesion in some highly perfused tissue locations may require twice as much power as an identically-sized lesion in less highly perfused locations. While a variety of approaches for achieving such complete, thorough, and uniform heating of tissue have been proposed, most such approaches are somewhat complex. In general, many approaches for achieving uniform tissue heating have relied on slow, low power level, gradual heating of the tissue to avoid the formation of charred or otherwise desiccated, high radio frequency impedance regions within the target tissue. Such approaches, however, are complex, can result in undesirable prolongation of the treatment, and are not always successful.

For these reasons, it would be desirable to provide improved treatment methods, systems, and apparatus which allow for effective and efficient delivery of radio frequency energy to target tissue using electrodes disposed on bipolar devices. In particular, it would be desirable to provide such methods, systems, and apparatus which are useful with many or all bipolar surgical instruments which are now available or which might become available in the future. The methods, systems, and apparatus should be simple to implement and use, and should preferably reduce the complexity, cost, and treatment time required to achieve complete, thorough, and uniform heating and/or desiccation of the target tissue without charring the target tissue. At least some of these objectives will be met by the invention described hereinafter.

DESCRIPTION OF THE BACKGROUND ART

The heating of tissue with radio frequency current using the preferred bipolar surgical systems of the present invention is described in co-pending application Ser. Nos. 09/071,689 filed May 1, 1998 and 09/303,007 filed Apr. 30, 1999, the full disclosures of which are incorporated herein by reference. Radio frequency power apparatus and methods are described in U.S. Pat. Nos. 5,954,717, 5,556,396; 5,514,129; 5,496,312; 5,437,664; and 5,370,645; WO 95/20360, WO 95/09577, and WO 93/08757. Bipolar electrosurgical devices are described in U.S. Pat. Nos. 5,833,690; 5,797,941; 5,702,390; 5,688,270; 5,655,085; 5,662,680; 5,582,611; 5,527,313; 5,445,638; 5,441,499; 5,403,312; 5,383,876; 5,217,460; 5,151,102; 5,098,431; 4,043,342; and 4,016,886; Soviet Union Patent Publication SU 197711; and French Patent No. 598,149.

SUMMARY OF THE INVENTION

The present invention provides improved methods, systems, and apparatus for effective and efficient delivery of radio frequency (RF) energy to electrodes of bipolar surgical instruments disposed in treatment tissue for inducing hyperthermia and other purposes. The treatment region resulting from bipolar radio frequency treatment may be located anywhere in the body where hyperthermic exposure may be beneficial. The treatment region may comprise and/or be located in tissue of or surrounding the liver, kidney, lung, bowel, stomach, pancreas, breast, uterus, prostate, muscle, membrane, appendix, other abdominal or thoracic organs, and the like.

Treatments according the present invention will usually be effected by passing a radio frequency current through the treatment tissue region in a bipolar manner where paired treatment electrodes are employed to both form a complete circuit and to uniformly and thoroughly heat tissue therebetween. The paired electrodes will have similar or identical surface areas in contact with tissue and geometries so that current flux is not concentrated preferentially at either electrode (or electrode component such as a tissue-penetrating needle) relative to the other electrode(s). Such bipolar current delivery is to be contrasted with "monopolar" delivery where one electrode has a much smaller surface area and one or more "counter" or "dispersive" electrodes are placed on the patient's back or thighs to provide the necessary current return path. In the latter case, the smaller or active electrode will be the only one to effect tissue as a result of the current flux which is concentrated thereabout.

It has been found that the delivery of bipolar radio frequency power to electrodes disposed in tissue can, if the power is delivered for a sufficient time and/or at a sufficient power delivery level or flux, result in an increase in the electrical impedance between the electrodes and tissue. While such an increase in impedance is the natural consequence of tissue desiccation, it can be undesirable if it occurs prematurely since it results in an immediate fall-off of energy delivery (for a voltage limited radio frequency power source). Accordingly, the present invention relies on unique methods of radio frequency power delivery to uniformly and thoroughly heat the target tissue without charring the target tissue.

It is presently believed that the premature increase in electrode-tissue interface impedance may result from the formation of a thin gaseous or vapor layer over the electrode surfaces, apparently resulting from vaporization of water within the tissue as the temperature approaches the local boiling point. The thin gaseous layer appears to spread from an initial nucleation site to cover most or all of the electrode surfaces in a very short time period, resulting in the premature increase in electrode-tissue interface impedance which is very large when compared to the total system impedance prior to formation of the gaseous layer. The methods, systems, and apparatus of the present invention have been found to be useful and effective regardless of the actual mechanism which is responsible for the premature increase in impedance.

In a first particular aspect of the present invention, a method for heating a treatment region of tissue comprises introducing a bipolar surgical instrument, such as forceps, graspers, or the like, having first and second jaws with first and second electrode members within the treatment region. Tissue is grasped between the first and second jaws of the bipolar instrument. The electrode members are energized at a power level to deliver electrical energy to and heat tissue between the first and second electrode members. The power level is increased at a predetermined rate from an initial level. The initial level and predetermined rate are selected to avoid creating a vapor layer and to permit an impedance increase to occur as a result of complete tissue desiccation. The predetermined rate of power increase may be preselected by a user depending on the electrode sizes, the target tissue type, the degree of tissue perfusion, and the initial power level. Typically, the predetermined rate of power increase will be linear and increase at a rate in the range from 1 W/sec to 100 W/sec, preferably from 1 W/sec to 10 W/sec. Thus, the initial power level and predetermined rate of power increase allow for controlled delivery of bipolar radio frequency energy without premature impedance resulting from the formation of the thin gaseous layer. Furthermore, the increase in the power level at a predetermined rate from an initial level permits a natural impedance increase to occur as a result of complete tissue desiccation.

It may be further desirable to measure tissue impedance. The measured impedance may be compared to an impedance limit, wherein the impedance limit will be preselected by the user to indicate the impedance increase due to complete tissue desiccation, typically in the range from 50 ohms to 1000 ohms, preferably from 250 ohms to 750 ohms. If the measured impedance exceeds the impedance limit, the power delivery is automatically terminated. Additionally, the energizing of the electrode members and increasing the power level at a predetermined rate may be repeated at least once after termination until all the tissue between the electrode members is completely desiccated without charring the target tissue. Thus, complete heating and desiccation of tissue can be further optimized by monitoring tissue impedance and terminating the power delivery at a maximum impedance limit. As an added safety feature, the power delivery may also be automatically terminated after a preset amount of time, typically after period of 5 minutes, regardless of measured impedance so as to avoid overheating of the target tissue or unwanted heating of adjacent tissue. Alternatively, the power delivery may be manually terminated with the use of a radio frequency off switch that will immediately terminate power delivery.

In general, electrode members are energized with radio frequency energy supplied as a radio frequency current using a controlled voltage supply. The use of such radio frequency power sources is preferred because the limited voltage available decreases the likelihood of arcing or sparking from the electrode members into the tissue. Usually, the power supply will be operated at a level which depends on the electrode sizes, the target tissue type, and the degree of tissue perfusion. Typically, the power supply will provide power in the range from 5 W to 150 W, preferably from 10 W to 80 W, and a frequency in the range from 100 kHz to 2 MHz, preferably from 400 kHz to 500 kHz, during all phases of the above-described methods. The electrode members are energized typically for a time less than 5 minutes, preferably for a time in a range from 10 seconds to 1 minute. Additionally, at least one of the electrode members may comprise a plurality of tissue penetrating elements, the tissue penetrating elements engaging the tissue before the electrode members are energized.

In further aspects of the present invention, systems are provided which comprise an electrosurgical power supply, typically a radio frequency generator, in combination with written, electronic, or other instructions setting forth any of the methods set forth above.

In still another aspect of the present invention, computer programs embodied in a tangible medium, such as a floppy disk, compact disk, tape, flash memory, hard disk memory, read only memory (ROM), internet/modem instructions, and the like, may set forth any of the methods described above, in computer-readable code. Such computer programs are useful with digital controllers which may be built into a radio frequency generator or other electrosurgical power supply according to the present invention. Alternatively, such programs may be useful with general purpose computers, which can be interfaced with conventional electrosurgical power supplies for the control thereof according to any of the methods of the present invention.

In a still further aspect of the present invention, radio frequency generators are provided which comprise a radio frequency power source having both a controlled voltage output and a standard bipolar connection for bipolar forceps or the like. The radio frequency generator will further comprise means for automatically increasing power delivered to the bipolar connection. The increasing means increases the power at a predetermined rate from an initial level. The initial level and predetermined rate avoid formation of a vapor layer while permitting an impedance increase to occur as a result of complete tissue desiccation. The predetermined rate of power increase will be preselected by a user depending on the electrode sizes as well as the initial power level, typically being linear and increasing at a rate in the range from 1 W/sec to 100 W/sec, preferably from 1 W/sec to 10 W/sec.

The increasing means may initiate a cycle where it measures an impedance of tissue, compares the measured impedance to an impedance limit, and increases the power level based on the predetermined rate of power increase if the measured impedance does not exceed the impedance limit. The impedance limit is selected to indicate the impedance increase due to complete tissue desiccation, typically in the range from 50 ohms to 1000 ohms, preferably from 250 ohms to 750 ohms. Furthermore, the increasing means repeats the cycle and need only be activated once for continual cycling. The increasing means may comprise a programmable digital controller, a control program embodied in a tangible medium, or other means for automatically increasing power delivered by the generator. In particular, the digital controller or other increasing means can be programmed to implement any of the methods described above independent of operator intervention.

The radio frequency generator may further comprise a user interface for inputting the rate of power increase, the initial power level, and an impedance limit. The user interface may further comprise a front panel display that displays at least one of the following: a real-time impedance, total energy delivered, and/or instantaneous power delivered. Optionally, the user interface may comprise an audible alarm which indicates the current delivery of power in addition to appropriate generator status signals.

DESCRIPTION OF THE SPECIFIC EMBODIMENTS

Figure 1:
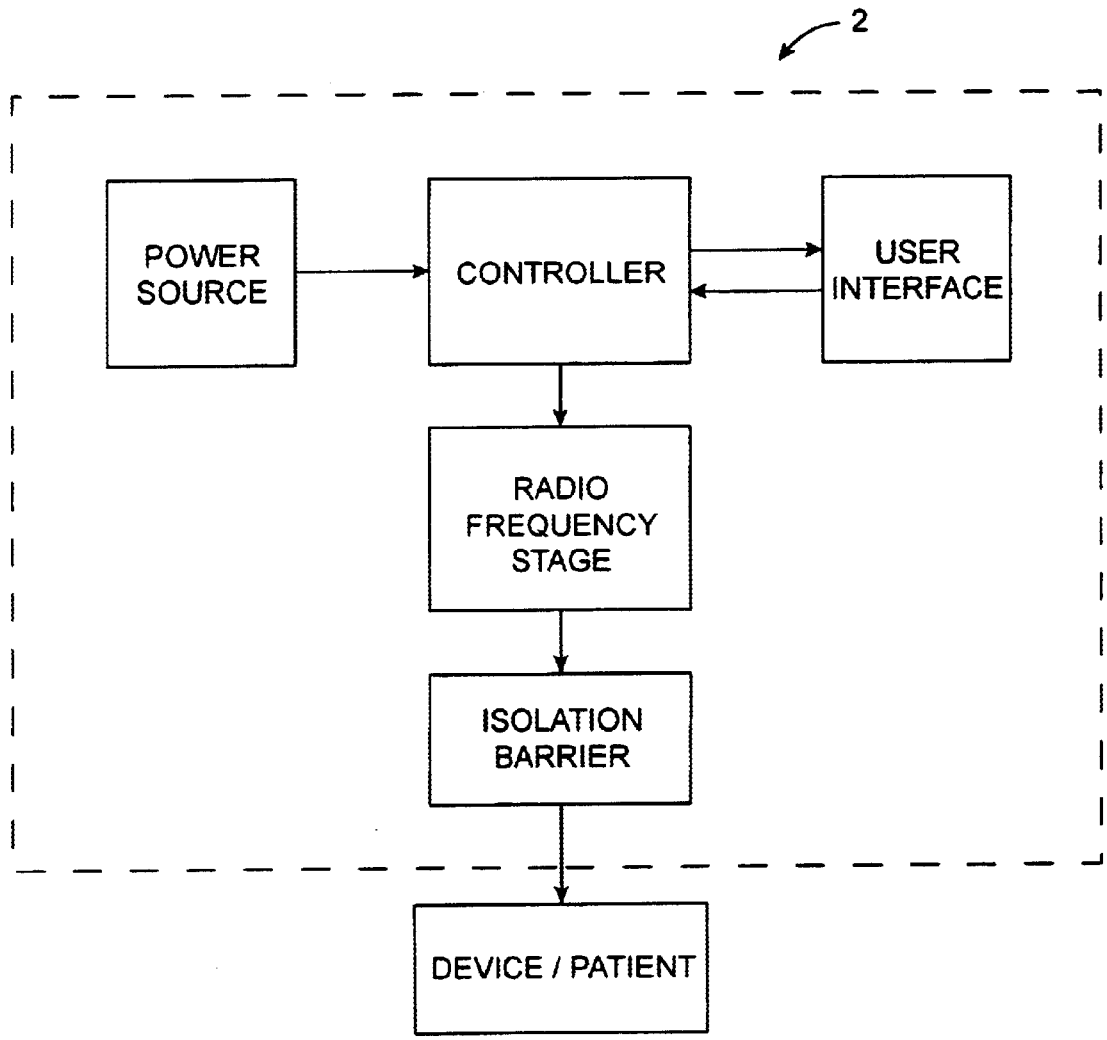
FIG. 1 is a functional flow diagram illustrating an overview of the bipolar radio frequency power apparatus of the present invention.

Methods, systems, and apparatus according to the present invention will rely on the controlled delivery of radio frequency power to electrode members of a bipolar surgical instrument placed at or within a treatment tissue region of a patient for heating and/or desiccating the treatment tissue. FIG. 1 illustrates a functional flow diagram of an overview of the bipolar radio frequency power apparatus of the present invention. The radio frequency power apparatus or generator 2 comprises a radio frequency power source having a controlled voltage output and a bipolar connection for bipolar forceps or the like. The desired radio frequency power may be supplied by a conventional general purpose electrosurgical power source operating at a frequency between 100 kHz to 2 MHz, preferably from 400 kHz to 500 kHz, with a conventional sinusoidal or non-sinusoidal wave form. Preferred power sources will operate at relatively low fixed voltages, typically from 100 V to 240 V. In all cases, current will be selected based on electrode sizes, target tissue type, and the degree of tissue perfusion, to provide an operating power in the range from 5 W to 150 W, preferably from 10 W to 80 W, for a time less than 5 minutes, preferably for a time in a range from 10 seconds to 1 minute.

Preferably, the radio frequency generator 2 will further incorporate means for automatically increasing power delivered to the bipolar connection. Such increasing means may comprise a programmable digital controller, such as a computer microprocessor, a control program embodied in a tangible medium, or other means for automatically increasing power delivered by the generator. Advantageously, the digital controller or other increasing means can be programmed to implement any of the methods described herein independent of operator intervention. The increasing means or controller will increase the power at a predetermined rate from an initial level, the initial level and predetermined rate avoiding formation of a vapor layer while permitting an impedance increase to occur as a result of complete tissue desiccation. Usually, the rate of increase is in the range from 1 W/sec to 100 W/sec, preferably from 1 W/sec to 10 W/sec.

The increasing means or controller may also initiate a cycle where it measures an impedance of tissue, compares the measured impedance to an impedance limit, and increases the power level based on the predetermined rate of power increase if the measured impedance does not exceed the impedance limit. The impedance limit is selected to indicate the impedance increase due to complete tissue desiccation, typically in the range from 50 ohms to 1000 ohms, preferably from 250 ohms to 750 ohms. Furthermore, the increasing means repeats the cycle and need only be activated once for continual cycling.

The generator 2 may further comprise a user interface for inputting the rate of power increase, the initial power level, and an impedance limit. The interface may also comprise a front panel display that displays at least one of a real time impedance, total energy delivered, and maximum power delivered. These display values are typically updated at 300 millisecond intervals. Additionally, the user interface may comprise an audible alarm for notifying the user that power is currently being delivered. The alarm usually beeps for short periods at 3 second intervals. Optionally, the user interface may have a radio frequency off switch that will immediately shut off delivery of radio frequency energy to the electrode members. This off switch serves as a back-up method to the impedance limit method to terminate power delivery.

The power source as controlled by the controller and/or user interface then connects to a radio frequency stage for delivery of energy to the patient via electrodes of the bipolar device. As an added safety feature, an isolation barrier is placed between the radio frequency delivery stage and the patient to minimize electrocution hazards. The radio frequency generator 2 is interfaced with the bipolar device/patient using a conventional cable. An exemplary radio frequency generator 2, as described above, having the capabilities suitable for the present invention is the PST Model 2150, which runs on a MOTOROLA® 68HC11 microprocessor with "C" programming language software, available from Perfect Surgical Techniques, Inc., Palo Alto, Calif., assignee of the present invention.

Figure 2:
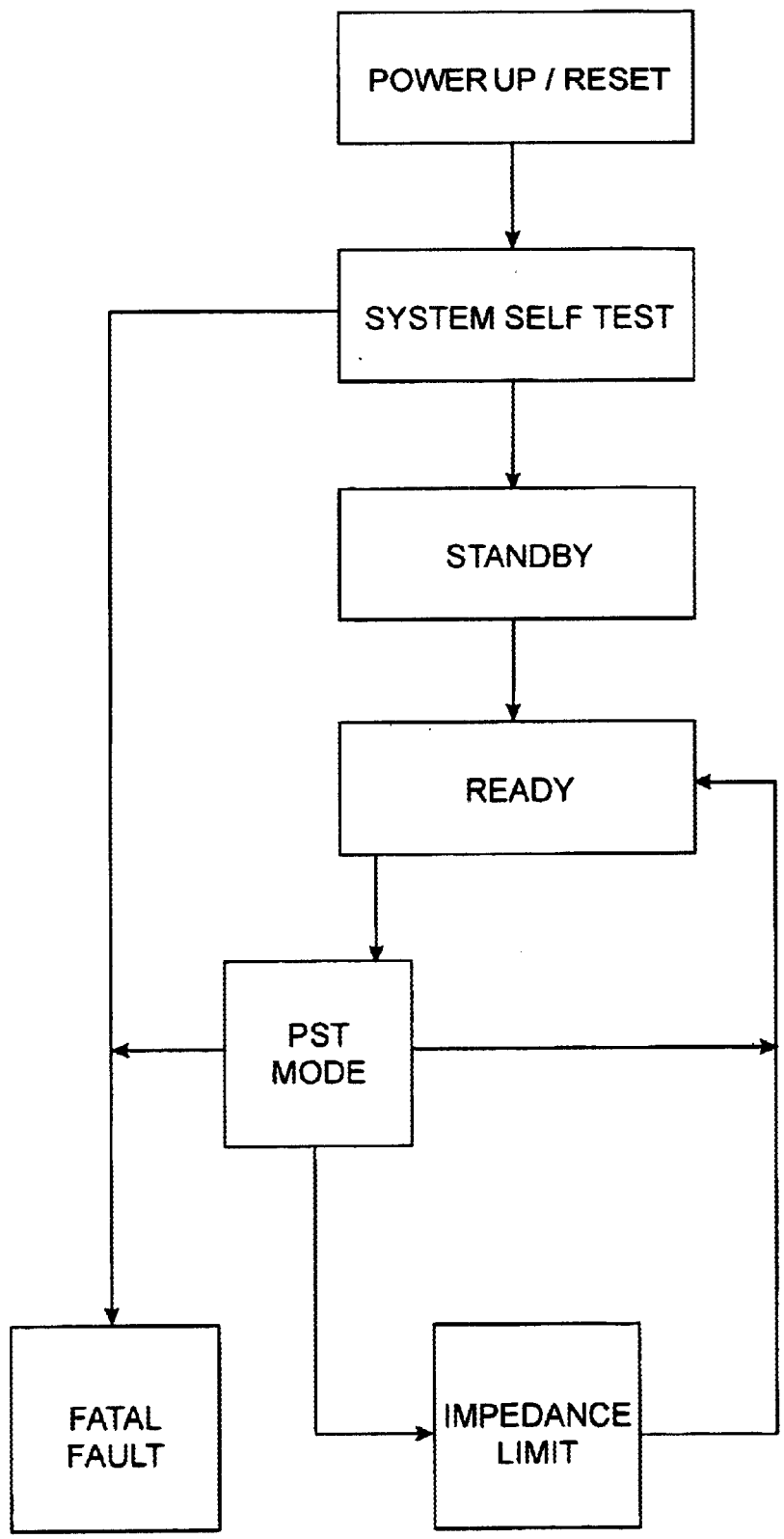
FIG. 2 is a flow chart illustrating method steps of the present invention which are implemented automatically by the digital controller of FIG. 1.

Referring now to FIG. 2, method steps of the present invention which are implemented automatically by the programmable digital controller of the radio frequency generator of FIG. 1 will be generally described. After power up/reset of the generator system, the system enters a self-test state to verify that system hardware and software are functioning normally. Failure of any self-test causes the system to enter a fatal fault state, where it remains until the system is re-powered. After successful completion of all self-tests, the system automatically enters the standby state. The standby state is a non-finctional state and no radio frequency energy can be delivered in this state. The system remains in the standby state until the user requests a change to an operational mode by pressing the ready switch. While in the ready state, the system can be commanded to deliver controlled bipolar radio frequency power via a PST mode, which is described in more detail below, or a standard bipolar mode.

Figure 3:
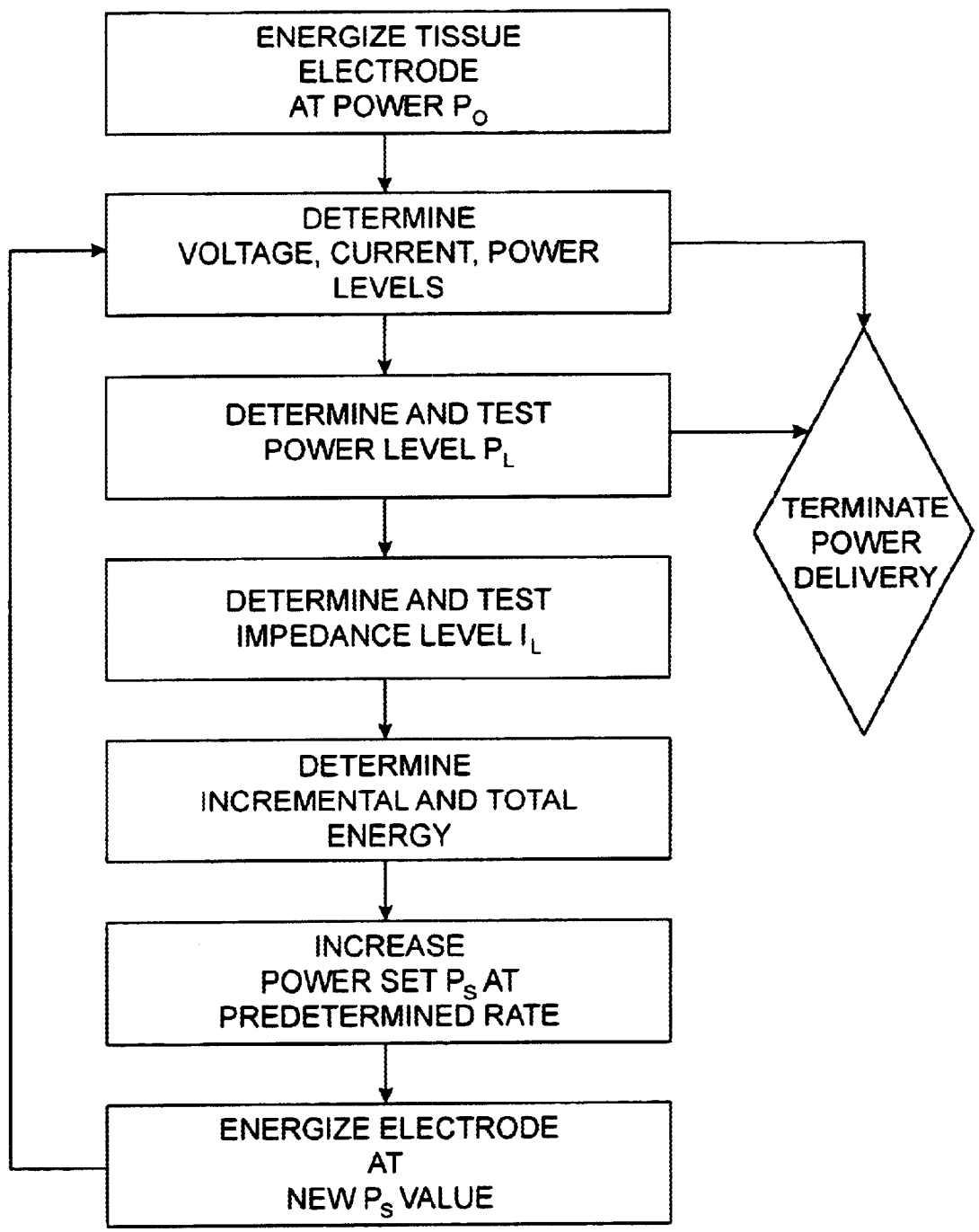
FIG. 3 is a flow chart illustrating method steps of the present invention which are implemented automatically in the PST mode of FIG. 2.
Figure 6A:
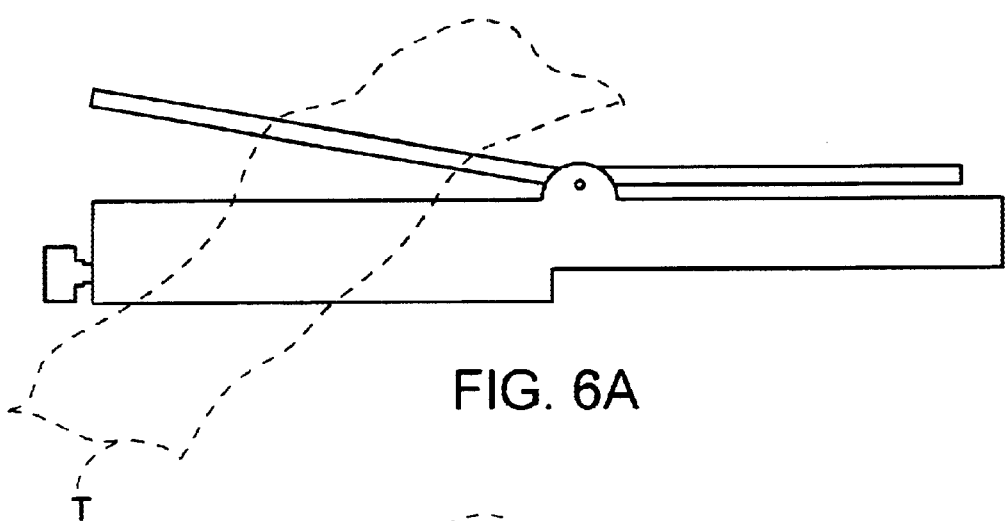
FIGS. 6A–6C illustrate use of the of the bipolar instrument of FIGS. 4A–4C in treating a target tissue region according the methods of the present invention.

FIG. 3 is a flow chart illustrating method steps of the present invention which are implemented automatically in the PST Mode. Initially, a method for heating a treatment region of tissue comprises introducing a bipolar surgical instrument having first and second jaws with first and second electrode members within the treatment region (FIG. 6A). Tissue is grasped between the first and second jaws of the bipolar instrument (FIG. 6C). The electrode members are then energized at an initial power level $P_o$ in the PST mode to deliver electrical energy to and heat tissue between the first and second electrode members.

As seen in FIG. 3, voltage, current, and power levels are determined and the power level is tested at 20 millisecond intervals. If the power level read is more than 5 watts greater than a power set value, the system automatically terminates power delivery and enters the fault state, where it remains until the system is re-powered. At this same interval, tissue impedance is measured and tested by comparing the measured impedance to an impedance limit, the impedance limit typically being in the range from 50 ohms to 1000 ohms. If the measured impedance exceeds the impedance limit, the power delivery is automatically terminated and the system returns to ready state. Incremental and total energy levels are also calculated during this 20 millisecond interval. If the impedance limit is not exceeded, the power set level is increased at a predetermined rate from the initial level, wherein the initial level and predetermined rate are selected to avoid creating a vapor layer and to permit an impedance increase to occur as a result of complete tissue desiccation. Typically, the predetermined rate is from 1 W/sec to 100 W/sec, and the electrode members are energized at this increased power set value at 100 millisecond intervals.

The above described sequence of steps are automatically repeated until all the tissue between the first and second electrode members is completely desiccated with minimal charring to the treatment tissue. The electrodes are energized with bipolar radio frequency current supplied with a controlled voltage power supply, as described in FIG. 1. In some instances, at least one of the electrode members may comprise a plurality of tissue penetrating elements, the tissue penetrating elements engaging the tissue before the electrode members are energized (FIG. 6C). Furthermore, energizing of the electrode members and increasing the power level steps may be repeated at least once after power delivery termination. As an added safety feature, the system will also terminate power delivery in the PST mode after a preset amount of time, typically after a period of 5 minutes, at which time it will return to the ready state, to ensure that the treatment tissue is not overheated.

Figure 4A:
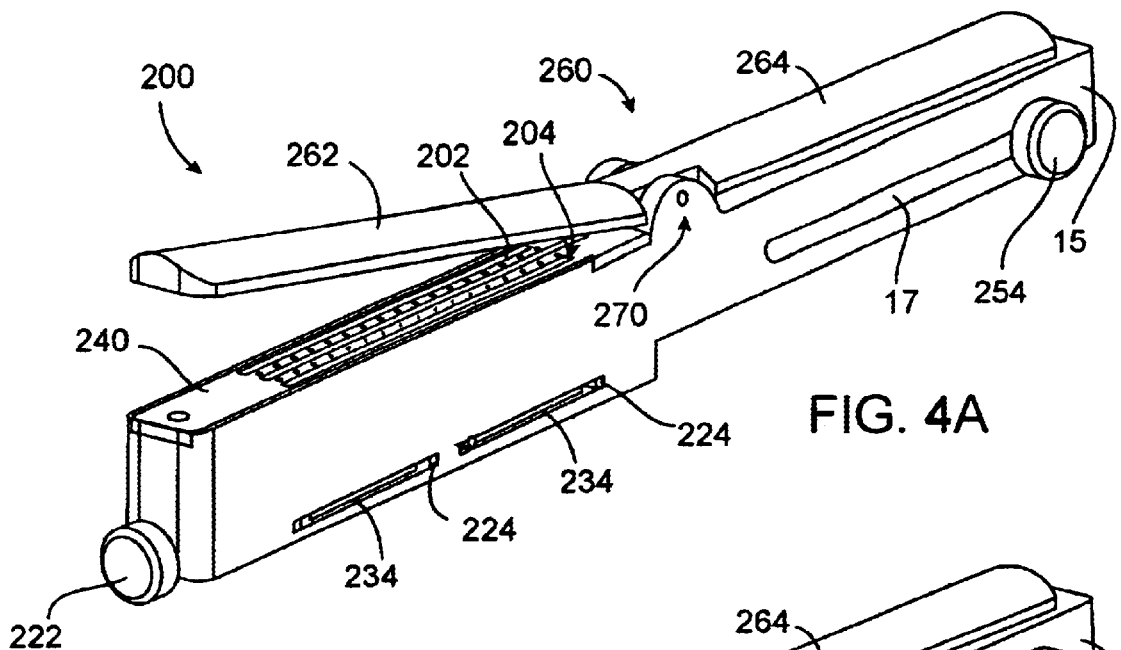
FIGS. 4A–4C illustrate an exemplary bipolar surgical instrument which may be employed in the methods and systems of the present invention.
Figure 4B:
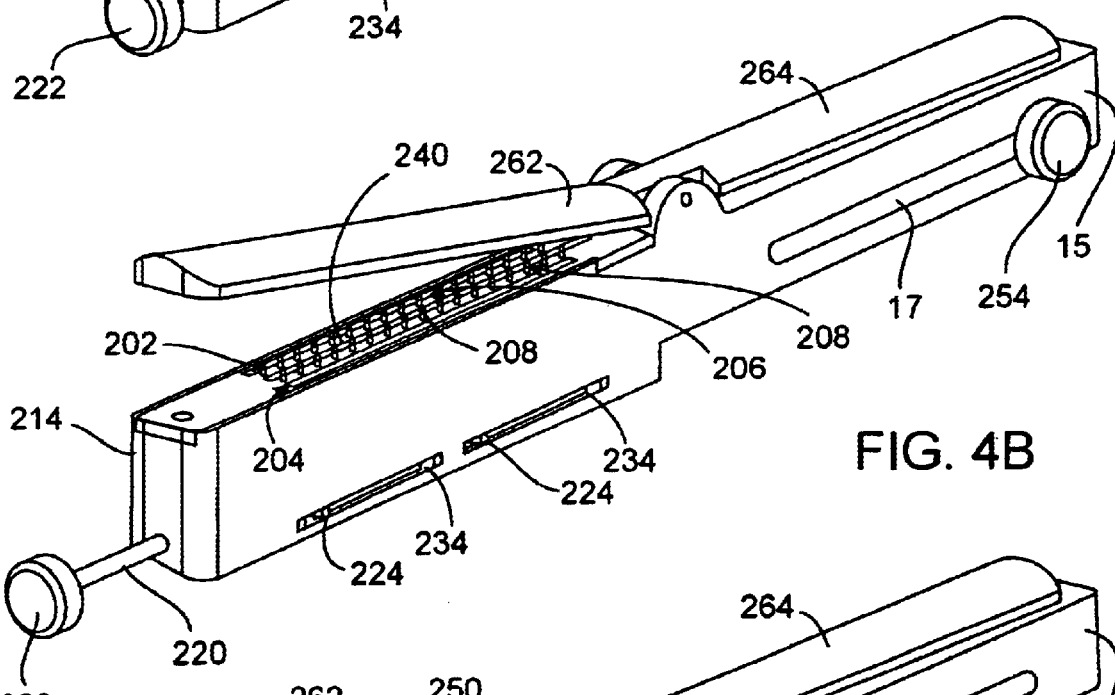

Referring now to FIGS. 4A–4C and 5, a preferred bipolar surgical instrument with electrode members for use with the methods and apparatus of the present invention will be described. A bipolar surgical instrument 200 having an arrangement of surface electrodes 202 and 204 and rows 206 and 208 of tissue-penetrating electrodes, is illustrated. The rows 206 and 208 of tissue-penetrating electrodes are mounted in an electrically conductive insert which in turn is mounted in a cavity in instrument housing 214. The insert is free to reciprocate within the cavity and is mounted on a rod 220 having a knob 222 and a pair of pins 224. The rod 220 is received in a channel in the bottom of the insert, and the pins 224 extend outwardly through a pair of inclined slots in the insert and then through slots 234 in the side of the housing 214. In this way, axial movement of the rod 220 (caused by pulling or pushing on the knob 222) can cause the insert to rise or lower within the cavity. In turn, this causes the tissue-penetrating electrodes 206 and 208 to reciprocate between a lowered configuration (FIG. 4A) and a raised configuration (FIG. 4B).

Figure 4C:
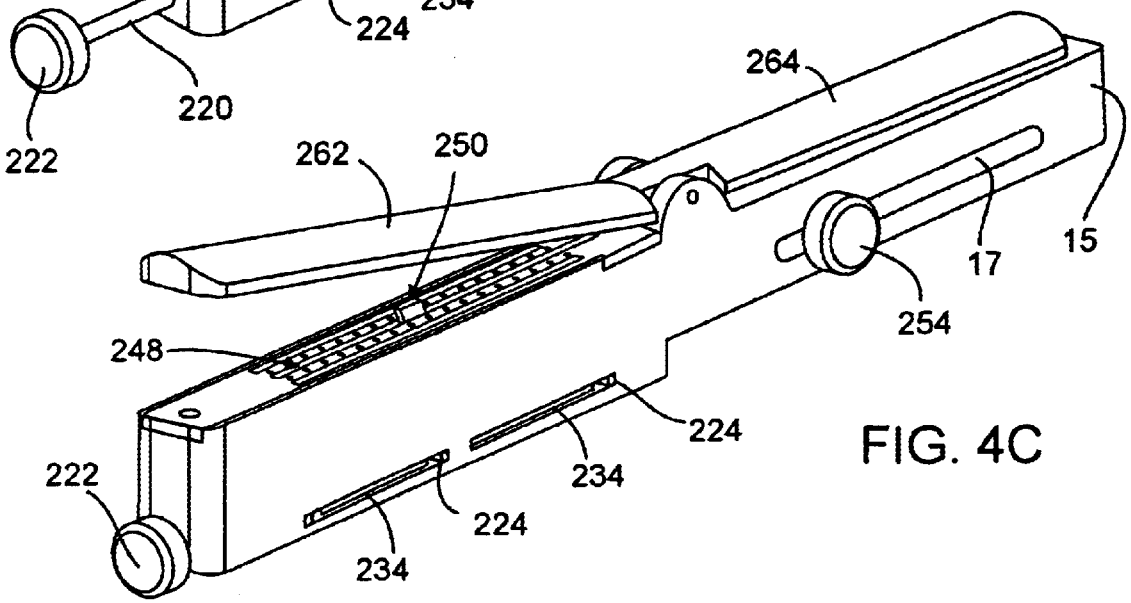

The outer electrodes 202 and 204 are received in a plate 240 which is mounted over the cavity in housing 214. The plate 240 has a pair of slots for receiving the electrodes 202 and 204, respectively. Additionally, plate 240 has a plurality of holes along lines spaced inwardly from the slots. Additionally, a channel 248 is formed along the center line of the plate 240 to receive a cutting blade 250, as best seen in FIG. 4C.

Figure 5:
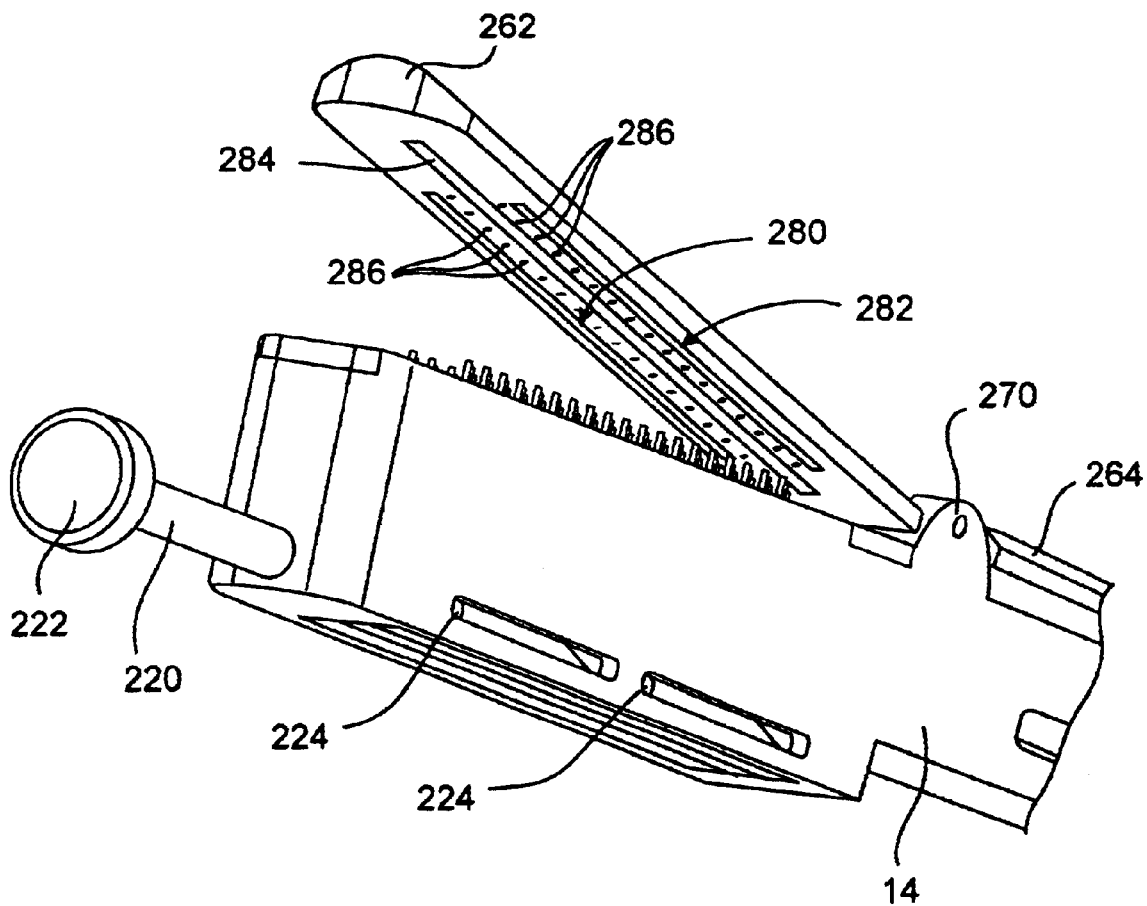
FIG. 5 is an alternative view of the instrument of FIGS. 4A–4C.

The housing 214 forms a lower jaw structure and a hinged lever assembly 260 forms the upper jaw structure. The lever 260 includes a cover section 262 and a lever arm section 264. A center or fulcrum section is secured between brackets 270 formed on the top of housing 214. In this way, the cover section 262 can be moved between an open configuration (FIG. 4A) and a closed configuration (FIGS. 6B and 6C) by lifting and lowering the lever arm section 264. The bottom of the cover section 262 is best illustrated in FIG. 5. The bottom includes a pair of top surface electrodes 280 and 282, a relief channel 284 for receiving the cutting blade 250, and relief holes 286 for receiving the upper tips of the tissue-penetrating electrodes when they are raised.

The cutting blade 250 is formed at a forward end of an elongate blade structure having a pair of knobs 254 at its opposite or proximal end. The body portion of the blade is received in a slot in a handle portion 15 of the housing 214. The knobs extend on a connecting shaft out through a slot 17 in the handle 15. Thus, the blade can be advanced and retracted axially by moving the knob 254 from a retracted configuration (FIGS. 4A and 4B) to an advanced configuration (FIG. 4C). The knob is disposed in the channel 248 so that it will pass and cut through tissue which has been previously desiccated by applying radio frequency energy through the electrode structures of instrument 200, as described below.

Figure 6B:
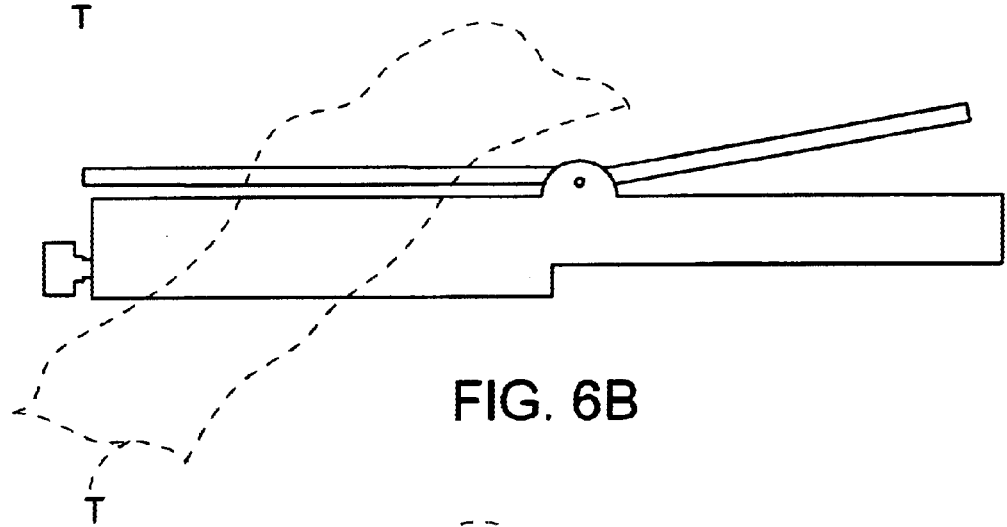
Figure 6C:
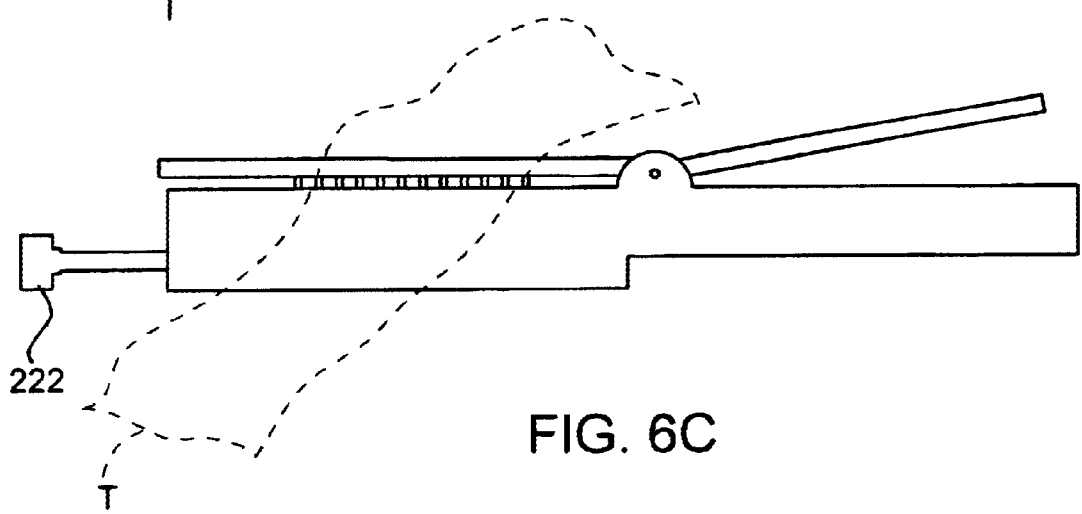

Referring now to FIGS. 6B–6C, a treatment region of tissue T may be located anywhere in the body where hyperthermic exposure may be beneficial. The treatment region may comprise and/or be located in tissue of or surrounding the liver, kidney, lung, bowel, stomach, pancreas, breast, uterus, prostate, muscle, membrane, appendix, other abdominal or thoracic organs, and the like. Initially, the cover 262 will be open and the tissue-penetrating electrodes 206 and 208 will be retracted into the housing 14 (FIGS. 6A and 4B). After introducing a bipolar surgical instrument 200 into a patient and positioning a target tissue structure between the open cover 262 and plate 240 of the housing 14, as shown in FIG. 6A, the cover can be closed grasping the tissue (as shown in FIG. 6B). The tissue-penetrating electrodes are then raised by pulling knob 222 (FIG. 6C), causing the electrodes 206 and 208 to engage the tissue before energizing the electrodes. Surface electrodes 202, 204, 280, and 282 in contrast, will compress on opposite sides of the tissue, but will not penetrate into the tissue.

Radio frequency current will then be applied to the tissue according to the PST mode protocols as described above, with the surface electrodes being attached to one pole of radio frequency generator 2 and the tissue-penetrating electrodes being attached to the other pole. The electrical field will thus be concentrated between an outermost pair of surface electrodes (202/280 or 204/282) and the adjacent tissue-penetrating electrodes (206 or 208). Alternatively, the pole attachments of the radio frequency generator may be configured to provide an electrical field that is concentrated between the surface electrodes (202 and 204) or between the rows of tissue penetrating electrodes (206 and 208). The tissue may be completely desiccated with all the advantages of the use of a tissue-penetrating electrode energized by a bipolar radio frequency generator as described above. After complete desiccation is achieved, the blade 250 can be advanced to cut through the parallel segments of desiccated tissue which have been formed.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for heating a treatment region of tissue, said method comprising:

introducing a bipolar surgical instrument having first and second jaws with first and second electrode members within the treatment region;

grasping tissue between the first and second jaws;

energizing the electrode members at a power level to deliver electrical energy to and heat tissue between the first and second electrode members; and increasing the power level at a predetermined rate from an initial level, wherein the initial level and predetermined rate are selected to avoid creating a vapor layer and to permit an impedance increase to occur as a result of complete tissue desiccation.

2. A method as in claim 1, further comprising measuring tissue impedance.

3. A method as in claim 2, further comprising comparing the measured impedance to an impedance limit, and automatically terminating power delivery if the measured impedance exceeds the impedance limit.

4. A method as in claim 3, wherein the impedance limit is selected to indicate the impedance increase due to complete tissue desiccation.

5. A method as in claim 3, wherein the impedance limit is in the range from 50 ohms to 1000 ohms.

6. A method as in claim 3, further comprising repeating the energizing and increasing steps at least once after termination until all the tissue between the first and second electrodes is completely desiccated without charring the treatment tissue.

7. A method as in claim 1, further comprising terminating power delivery automatically after a preset amount of time.

8. A method as in claim 1, wherein the electrode members are energized with radio frequency current.

9. A method as in claim 8, wherein the radio frequency current is supplied with a controlled voltage power supply.

10. A method as in claim 1, wherein at least one of the electrode members comprises a plurality of tissue penetrating elements, the tissue penetrating elements engaging the tissue before the electrode members are energized.

11. A method as in claim 1, wherein the power level is in a range from 5 W to 150 W.

12. A method as in claim 1, wherein the predetermined rate of power increase is in the range from 1 W/sec to 100 W/sec.

13. A method as in claim 1, wherein the electrode members are energized for a time less than 5 minutes.

14. A method as in claim 1, wherein the tissue comprises tissue of or surrounding the liver, kidney, lung, bowel, stomach, pancreas, breast, uterus, prostate, muscle, membrane, appendix, other abdominal organs, or other thoracic organs.

15. A system comprising:

a radio frequency generator; and instructions setting forth the method of claim 1.

16. A computer program embodied in a tangible medium, wherein the program sets forth a method according to claim 1.

17. A radio frequency generator comprising:

a radio frequency power source having a controlled voltage output and a bipolar connection for bipolar forceps having first and second jaws with first and second electrode members; and means for automatically increasing power delivered to the bipolar forceps;

wherein the increasing means increases the power at a predetermined rate from an initial level, the initial level and predetermined rate avoiding formation of a vapor layer while permitting an impedance increase to occur as a result of complete tissue dessication.

18. A radio frequency generator as in claim 17, wherein the increasing means initiates a cycle where it measures an impedance of tissue, compares the measured impedance to an impedance limit, and increases the power level based on the predetermined rate if the measured impedance does not exceed the impedance limit.

19. A radio frequency generator as in claim 18, wherein the impedance limit is selected to indicate the impedance increase due to complete tissue desiccation.

20. A radio frequency generator as in claim 18, wherein the impedance limit is in the range from 50 ohms to 1000 ohms.

21. A radio frequency generator as in claim 18, wherein the increasing means repeats the cycle.

22. A radio frequency generator as in claim 18, wherein the increasing means is activated only once for continual cycling.

23. A radio frequency generator as in claim 17, further comprising a user interface for inputting the rate of power increase, the initial power level, and an impedance limit.

24. A radio frequency generator as in claim 23, wherein the user interface further comprises a front panel display that displays at least one of real-time impedance, total energy delivered, and instantaneous power delivered.

25. A radio frequency generator as in claim 23, wherein the user interface further comprises an audible alarm which indicates the delivery of power.

26. A radio frequency generator as in claim 17, wherein the predetermined rate of power increase is in the range from 1 W/sec to 100 W/sec.

27. A radio frequency generator as in claim 17, wherein a time of power delivery is less than 5 minutes.

28. A radio frequency generator as in claim 17, wherein the power source operates at a frequency in the range from 100 kHz to 2 MHz and a power level in the range from 5 W to 150 W.

29. A radio frequency generator as in claim 17, wherein the increasing means comprises a programmable digital controller.

30. A radio frequency generator as in claim 17, wherein the increasing means comprises a control program embodied in a tangible medium.

* * * * *